United States Patent

Hasegawa et al.

[11] Patent Number: 4,705,755
[45] Date of Patent: Nov. 10, 1987

[54] APPARATUS FOR COLLECTING LYSOZYME FROM EGG WHITE BY ADSORPTION

[75] Inventors: Mineo Hasegawa, Hachioji; Kitao Ozaki, Fuchu, both of Japan

[73] Assignee: Kewpie Kabushiki Kaisha, Tokyo, Japan

[21] Appl. No.: 756,552

[22] Filed: Jul. 19, 1985

Related U.S. Application Data

[63] Continuation of Ser. No. 445,716, Nov. 30, 1982, abandoned.

[30] Foreign Application Priority Data

May 31, 1982 [JP] Japan .................................. 57-92513

[51] Int. Cl.[4] ........................ C12M 1/02; C12M 1/00; C12N 9/36; B01D 15/02
[52] U.S. Cl. .................................... 435/316; 435/287; 435/206; 435/815; 210/189; 210/268
[58] Field of Search ............... 435/287, 288, 206, 316, 435/803, 813, 814, 815, 816; 210/189, 268

[56] References Cited

U.S. PATENT DOCUMENTS

| | | | |
|---|---|---|---|
| 2,442,452 | 6/1948 | Alderton et al. | 435/206 |
| 2,744,840 | 5/1956 | Daniels et al. | 210/268 X |
| 3,515,643 | 6/1970 | Ghielmetti et al. | 435/815 X |
| 3,575,294 | 4/1971 | Hirowatari et al. | 210/189 |
| 3,634,229 | 1/1972 | Stanley, Jr. | 210/189 X |
| 4,033,820 | 7/1977 | Brouillard | 435/288 |
| 4,104,125 | 8/1978 | Takechi et al. | 435/815 X |
| 4,280,904 | 7/1981 | Carlson | 210/189 X |
| 4,552,845 | 11/1985 | Reid | 435/206 |

FOREIGN PATENT DOCUMENTS

| | | | |
|---|---|---|---|
| 2401627 | 8/1974 | Fed. Rep. of Germany | 210/189 |
| 1261082 | 1/1972 | United Kingdom | 210/189 |

OTHER PUBLICATIONS

Miller et al., "Phase Contacting and Liquid–Solid Processing", In: Perry et al, Chemical Engineers Handbook, 5th Ed (1973), New York, McGraw Hill, pp. (19-38-)-(19-41).

Peters et al, Plant Design and Economics for Chemical Engineers, 3rd Ed. (1980), New York, McGraw Hill, pp. 547-551.

Danes, "The Batch Application Process & Ion Exchange Unit Operation-I", Chemical Engineering Science, vol. 26 (1971), pp. 1277-1287.

Primary Examiner—Robert J. Warden
Assistant Examiner—Randall E. Deck
Attorney, Agent, or Firm—Oblon, Fisher, Spivak, McClelland & Maier

[57] ABSTRACT

A batch system apparatus for collecting lysozyme from egg white by adsorption on an ion-exchange resin, which includes a lysozyme adsorption tank, equipped therein with a stirring mechanism for stirring an egg white solution and an ion-exchange resin, having a strainer provided in a lower portion thereof, having liquid discharge pipes connected thereto at a position below the strainer, preferably at the bottom of the tank, and at the side wall above the strainer at a height such that the resin when left at rest will not overflow, respectively, and further having a resin discharge pipe connected thereto at the lower portion of the side wall, above and in the vicinity of the strainer; a positive displacement pump connected to the liquid discharge pipes for transferring the egg white solution after removal of lysozyme to a reservoir tank; and a centrifugal pump connected to the resin discharge pipe for transferring the mixture of the resin and water to a separate tank, whereby collection by adsorption can be made simple, convenient for use and also suitable for a small-quantity treatment.

7 Claims, 1 Drawing Figure

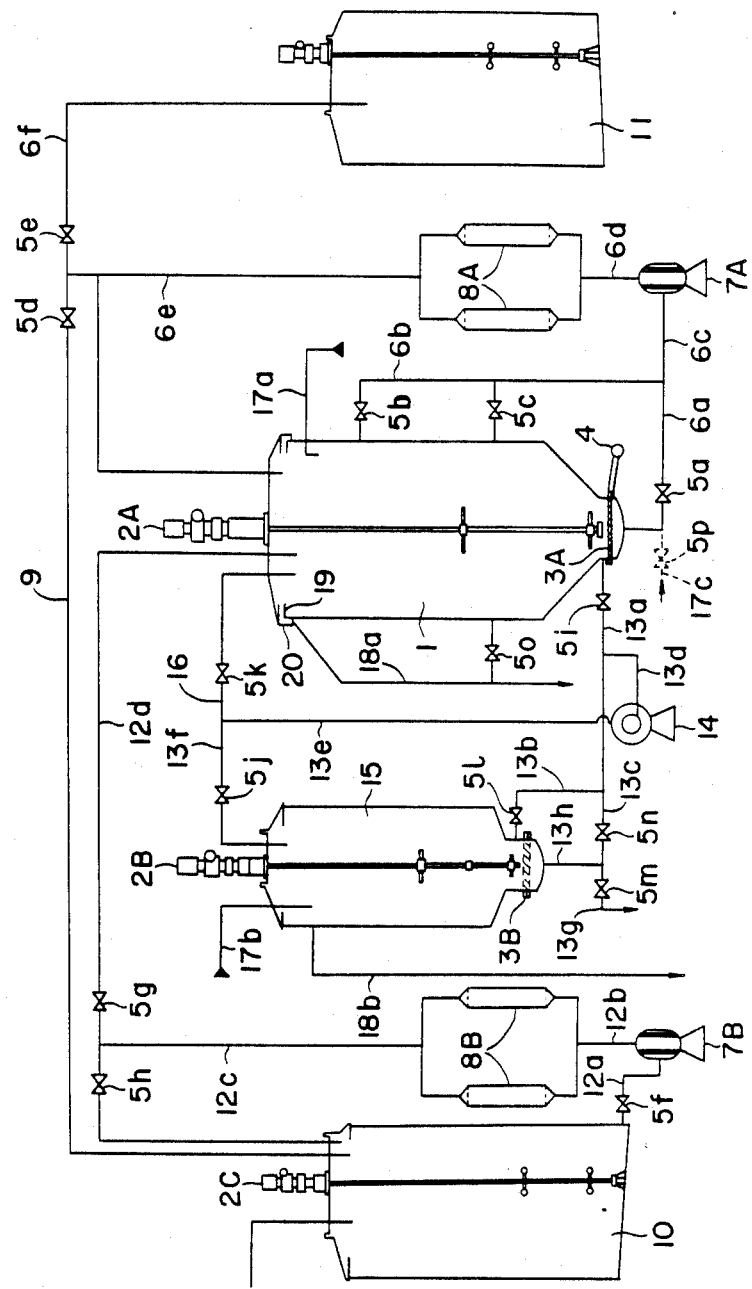

APPARATUS FOR COLLECTING LYSOZYME FROM EGG WHITE BY ADSORPTION

This application is a continuation of application Ser. No. 445,716, filed Nov. 30, 1982, now abandoned.

FIELD OF THE INVENTION

This invention relates to apparatuses for collecting lysozyme known as a bacteriolytic enzyme present in egg white in trace amounts from egg white by adsorption on an ion-exchange resin. More particularly, the present invention pertains to the structural organization of an apparatus of this character for collecting lysozyme according to the batch system ion-exchange process.

BACKGROUND OF THE INVENTION

In the art of ion-exchange reaction with the use of a resin, the batch process is inefficient and therefore recourse is made more frequently to the continuous columnar process (fixed bed ion-exchange system). However, the columnar process involves some drawbacks. One is that a large amount of a resin must be used. In addition, because of insufficient contact of the resins with the feed solution, the apparatus must have a complicated structure to cause sufficient contact with the feed solution. Thus, the columnar process is not suitable for application in treatment of a small quantity of feed solution. Accordingly, it is preferable to adopt the batch process in order to reliably collect lysozyme by adsorption at low cost, which lysozyme is contained only in a quantity of about 0.3% in egg white. In the case of the batch process, however, there is the problem of inefficiency as mentioned above involving, for example, cumbersome operations such as delivery of resins or feed solution from the adsorption tank to another tank. For solving this problem, employment of pressurized air for stirring or delivery of resins or treated solution has been investigated, but this attempt has proved to result in increase of the cost. In conclusion, under the present state of the art, no suitable device in either columnar or batch system has been developed for adsorbing or extracting lysozyme economically by treatment of a small amount of the egg white starting material.

In view of the background as described above, we have made studies to develop an apparatus for collecting by adsorption lysozyme in egg white which is convenient for use with easy handling, efficient, suitable for a small-quantity treatment and yet inexpensive. Especially we have placed emphasis on the two points that the adsorption tank of lysozyme should be made to have a construction such that it can be used as it is as the lysozyme extraction tank and that delivery of resins or solutions should be performed by a mechanism without the need of pressurized air. Thus, starting with a study on the quantities of resins required, followed by various tests, the apparatus according to the present invention has been reduced to practice.

SUMMARY OF THE INVENTION

An object of the present invention is to provide an apparatus for collecting by adsorption lysozyme in egg white which is convenient for use with easy handling, efficient, suitable for a small-quantity treatment and yet is inexpensive.

The present invention having accomplished the above object provides an apparatus for collecting lysozyme in egg white by adsorption, comprising:

a lysozyme adsorption tank, equipped therein with stirring means for stirring an egg white solution and an ion-exchange resin, having a strainer provided in a lower portion thereof, having liquid discharge pipes connected thereto at a position below the strainer, preferably at the bottom of the tank, and at the side wall above the strainer at a height such that the resin when left at rest will not overflow, respectively, and further having a resin discharge pipe connected thereto at the lower portion of the side wall, above and in the vicinity of the strainer;

a positive displacement pump connected to the liquid discharge pipes for transferring the egg white solution after removal of lysozyme to a reservoir tank; and a centrifugal pump connected to the resin discharge pipe for transferring the mixture of the resin and water to a separate tank.

BRIEF DESCRIPTION OF THE DRAWING

In the drawing, the single FIGURE is a schematic flow chart of an example of an apparatus constituting a preferred embodiment of the present invention.

DETAILED DESCRIPTION OF THE INVENTION

The present invention will now be described in detail with respect to the preferred embodiment thereof illustrated in the drawing.

Referring to the drawing, the principal components of the apparatus illustrated therein are an adsorption tank 1, a resin tank 15, a receptacle 10 for egg white to be treated, and a crystallization tank 11. In addition, positive displacement pumps 7A and 7B, a centrifugal pump 14 and associated strainers 8A,8A and 8B, 8B, respectively are provided. These components are connected by way of piping and valves as shown and as described hereinafter.

The vertical type adsorption tank 1 is equipped with a two-blade system variable-speed agitator 2A which extends vertically downward from the top of the tank, and a strainer 3A of 60-mesh size is mounted at the lower portion thereof so as to be freely detachable from the outside. A lever 4 for dismantling the strainer is provided. Below the strainer 3A and at the bottom of the adsorption tank 1, there is connected a liquid discharge pipe 6a having a valve 5a, which joins a liquid discharge pipe 6b extending downward from the side wall of the adsorption tank with the valves 5b and 5c into a liquid discharge pipe 6c to be connected to the intake port of the positive displacement pump 7A.

The delivery port of this pump 7A is connected via a liquid discharge pipe 6d to the strainers 8A, 8A and thereafter to a liquid discharge pipe 6e branched into two systems of piping, one reaching, via the liquid discharge pipe 9 having a valve 5d, the receptacle 10 for egg white to be treated as a reservoir, and the other reaching, via a liquid discharge pipe 6f having a valve 5e, the crystallization tank 11. The liquid discharge outlet of the valve 5b is at a position higher than the middle part of the side wall of the adsorption tank 1, while the outlet of the valve 5c is below that of the valve 5b at a height such that the resin settling on the strainer 3A in the adsorption tank 1 when it is brought to a stationary state by stopping the stirring by the agitator 2A will not overflow out of the adsorption tank 1.

The receptacle 10 for egg white to be treated is also equipped with an agitator 2C, and a starting-material feed pipe 12a is connected to the bottom part thereof by way of a valve 5f and is connected to the intake side of the positive displacement pump 7B. The delivery side of the pump 7B is connected via a starting-material feed pipe 12b, the strainers 8B, 8B, a starting-material feed pipe 12c, and a starting-material feed pipe 12d having a valve 5g to the upper part of the adsorption tank 1. During the feeding operation, a valve 5h in a pipe connecting the feed pipe 12c and the upper part of the receptacle 10 is closed.

At the lower side wall portion of the adsorption tank 1, but higher than the strainer 3A, there is provided in the vicinity of the strainer a resin discharge pipe 13a having a valve 5i. This resin discharge pipe 13a may have a tip inserted into the adsorption tank with its mouth portion bent downwardly (toward the strainer). It is necessary to keep the tip of the pipe away from contact with the tip of the agitator 2A in making such an installation. The resin discharge pipe 13a joins resin discharge pipes 13b and 13c as hereinafter described into a resin discharge pipe 13d which is connected to the intake side of a centrifugal pump 14, the delivery side of which is connected via a resin discharge pipe 13e and a resin discharge pipe 13f having a valve 5j to the upper part of the resin tank 15 and is also connected through a pipe 16 having a valve 5k to the upper part of the adsorption tank 1. During discharging of the resin, the valve 5k is closed.

The vertical resin tank 15, which is smaller than the adsorption tank 1, is equipped with a two-blade system variable-speed agitator 2B extending downward vertically from the upper part thereof and is also provided at its lower portion with a strainer 3B of 60-mesh size so as to be freely detachable from the outside. At the lower portion of the resin tank 15 in the vicinity of the upper part of the strainer 3B, there is provided a resin discharge pipe 13b having a valve 5l. Below the strainer 3B, that is, at the bottom of the resin tank 15, there is provided a resin discharge pipe 13h, which is branched into a water discharge pipe 13g having a water discharge valve 5m and a resin discharge pipe 13c having a valve 5n. The resin discharge pipes 13b and 13c are joined together and to the above described resin discharge pipes 13a and 13d connected to the intake side of the centrifugal pump 14. The delivery side of the pump 14 can be connected through the resin discharge pipe 13e and via the resin discharge pipe 16 having a valve 5k to the upper part of the adsorption tank 1 by closing the valve 5j and opening the valve 5k.

Water supply pipes 17a and 17b are provided respectively at the upper parts of the adsorption tank 1 and the resin tank 15, which are also provided with drain pipes 18a and 18b, respectively. Around the upper end of the adsorption tank 1, there is provided an annular drain trough 19 which serves to collect water overflowing when the adsorption tank 1 is being fed with feeding water through the water supply pipe 17a. This drain trough 19 is connected to the drain pipe 18a so that liquid is drained from the adsorption tank 1 whenever the level of liquid in the tank reaches the trough 19. The drain pipe 18a is also connected through a valve 5o to a lower part of the adsorption tank 1. Furthermore, a lid 20 is placed over the adsorption tank 1 so that the overflowing water will not easily flow to the outside of the drain trough 19.

The positive displacement pumps 7A and 7B used in the present invention may be exemplified typically by a rotary pump or a gear pump, referring generally to a pump in which a rotor is rotated within a casing to deliver a material to be delivered by compression of the volume within the casing. On the other hand, the centrifugal pump 14 refers to a pump in which a material to be delivered is energized by the centrifugal force of an impeller rotating within a casing, as exemplified by a cascade pump, a turbine pump or a vortex pump.

The apparatus according to a preferred embodiment of the present invention has a constitution as described above. Next, with the use of this apparatus, practical procedures for causing lysozyme to be adsorbed on an ion-exchange resin from egg white and then extracting the lysozyme from the resin will now be described with reference to the drawing.

First, a specific quantity of egg white solution is fed into the receptacle 10. After adjusting the pH of the egg white solution to around neutral by addition of an organic acid or the like, the agitator 2C is driven to homogenize the thick egg white in the egg white solution. Then, with opening of the valves 5f and 5g, the positive displacement pump 7B is driven to deliver under pressure the egg white solution through the strainer 8B, 8B into the adsorption tank 1. During this operation, the valves 5h, 5a, 5b, 5c, 5o and 5i are closed.

Within the adsorption tank 1, there is previously charged at the bottom thereof a specific quantity of a particulate weakly acidic cation exchange resin (e.g., 10 to 30 liter of resin per 100 kg of egg white solution). Therefore, on delivery of the entire amount of the above egg white solution, the agitator 2A is driven to stir and mix the egg white solution and the resin. The agitator is driven first at a low speed, and thereafter its speed is accelerated to a specific value while the state in the adsorption tank 1 is observed. After stirring has been carried out continuously for 2 to 5 hours in this state, the lysozyme in the egg white is adsorbed substantially completely onto the resin.

Then, the agitator 2A is stopped, and the mixture is left to stand for a while, whereby the egg white solution freed of lysozyme and the resin having adsorbed lysozyme are separated into upper and lower layers. While the resin settles on the strainer 3A, the egg white solution freed of lysozyme is delivered, by opening the valves 5b, 5c and 5d and operating the positive displacement pump 7A, through the liquid discharge pipes 6b, 6c, 6d, 6e and 9 to the receptacle 10. During this operation, the valve 5e is closed.

With progress of this delivery, the surface level of the egg white solution freed of lysozyme in the adsorption tank 1 is gradually lowered, whereby care is taken to avoid drawing out of the resin. When drawing out of the resin appears to be imminent, the positive displacement pump 7A is stopped, and the valves 5b and 5c are closed. Then, the valve 5a is opened and the positive displacement pump 7A is driven again to deliver under pressure the residual egg white solution freed of lysozyme through the liquid discharge pipes 6a, 6c, 6d, 6e and 9 to the receptacle 10.

In this case, in the adsorption tank 1, there is the strainer 3A at the lower portion thereof, on which the resin has settled. When an attempt is made to further deliver under pressure the egg white solution freed of lysozyme remaining on the resin by a measure such as air pressurization, a considerable high pressure is required. However, there is no possibility of any problems such as breaking of the strainer or overloading of the positive displacement pump because most of the egg white solution has been discharged through the liquid discharge pipe 6b and the egg white solution discharged through the discharge pipe 6a is of small amount.

Further, since a positive displacement pump with a high delivery pressure is empolyed, the total amount of the egg white solution can be drawn and transferred even in the presence of the intervening resin layer and strainer. If necessary, a small amount of water may be poured through the water supply pipe 17a into the adsorption tank 1 in order to carry out discharging through the liquid discharge pipe 6a to the receptacle side 10 similarly as described above, while washing away the foams of egg white adhering on the resin.

After delivery of the egg white solution freed of lysozyme to the receptacle 10 has thus been completed, the positive displacement pump 7A is stopped, and the valve 5a is closed. The egg white solution freed of lysozyme which is delivered to the receptacle 10 is taken out and provided for some other use.

In the adsorption tank 1 after delivery of the egg white solution freed of lysozyme to the receptacle 10 (in this case, functioning as a reservoir), the resin having adsorbed lysozyme remains on the strainer 3A, which resin is then delivered through the resin discharge pipes 13a, 13d, 13e and 13f to the resin tank 15. In carrying out this operation, water is first amply poured through the water supply pipe 17a into the adsorption tank 1, and the agitator 2A is driven to cause the resin to float in water. In this state, the valve 5i and then the valve 5j are opened, and the centrifugal pump 14 is driven to transfer the mixture of the resin and water to the resin tank 15. During this operation, the valves 5k, 5m, 5n and 5l are closed. By causing the resin to float amply in water, the resin can be transferred cleanly merely by discharging through the resin discharge pipe 13a. After all of the resin has been thus transferred, the agitator 2A and the centrifugal pump 14 are stopped, after which the valves 5i and 5j are closed. When necessary, the strainer 3A may be dismantled by operation of the lever 4 for washing.

Within the resin tank 15, water may be poured through the water supply pipe 17b onto the mixture of the resin and water delivered, and the resin may be washed when necessary by driving the agitator 2B, as water is drained through the drain pipe 18b. Further, after washing, extraction of lysozyme from the resin may be conducted in this resin tank 15. According to the present embodiment, however, the resin is returned to the adsorption tank 1, in which the operations of washing and extracting lysozyme are performed as described below.

That is, the resin having lysozyme adsorbed thereon which is placed in the resin tank 15 is transferred to the adsorption tank 1. First, the agitator 2B is driven, and then, with opening of the valves 5l and 5k of the resin discharge pipes 13b and 16, the centrifugal pump 14 is driven to transfer the mixture of the resin and water to the adsorption tank 1. During this operation, the valve 5j is closed. By such a circulating displacement (transfer) between the adsorption tank 1 and the resin tank 15, no damaging of the resin will be caused because the resin is caused to float in water by the stirring of the agitators 2A and 2B and use is made of a centrifugal pump 14 by which delivery (transfer) is carried out through centrifugal force. After completion of the transfer, the centrifugal pump 14 is stopped, and the valves 5l and 5k are closed.

Within the adsorption tank 1, the agitator 2A is continued to be driven, and water is poured through the water supply pipe 17a to wash thoroughly the resin while water is drained through the drain pipe 18a connected to the draining trough 19 at the lid 20. During this operation, the valve 5o is closed. After the washing is over, the agitator 2A is stopped, and the water supply is stopped. After the resin has settled on the strainer 3A, the valve 5o is opened to discharge water through the drain pipe 18a to obtain a specific water volume, and then sodium chloride or some other salt is added to provide a salt solution with a certain mole concentration or higher. Subsequently following conventional procedures, lysozyme adsorbed on the resin is extracted into the salt soluticn. The thus obtained salt solution having dissolved lysozyme therein is delivered by opening the valves 5c and 5e and driving the positive displacement pump 7A to the crystallization tank 11, wherein crystallization and purification are carried out in a conventional manner to provide the desired lysozyme. During this operation, the valve 5d is kept closed. The resin desorbed of lysozyme is transferred according to the same procedure as described above by driving the centrifugal pump 14 to the resin tank 15, wherein the resin may be subjected to suitable regeneration treatment or stocked as it is.

In delivering the resin together with water from the adsorption tank 1 to the resin tank 15, when the resin discharge pipe 13a tends to be clogged with the resin inclined to settle, a water supply pipe 17c (shown by broken line) equipped with a valve 5p may be separately provided to supply water through this water supply pipe, whereby clogging can be easily prevented by thinning the concentration of the resin dispersed at the lower portion of the adsorption tank 1 at the time of commencement of delivery. In washing the resin having lysozyme adsorbed thereon with water within the adsorption tank 1, the washing with water, i.e., backwashing, may be conducted by supplying water through the aforesaid water supply pipe 17c and the valve 5p, instead of washing with water by supplying water through the water supply pipe 17a.

In the apparatus according to the embodiment of the invention as described above, the adsorption tank 1 has a construction by which it can be used as an adsorption tank and also as means for extraction of lysozyme such as an extraction tank. In such a case, the resin tank 15 is used merely for temporary stocking or regeneration of the resin, and therefore it can be made of a compact size suitable for the required amount of the resin. However, the resin tank 15 is not limited to the construction of the above described example. For example, it can be made to have the same capacity and construction as the adsorption tank 1. In this case, the resin tank 15 can be used as the lysozyme extraction tank. Further, when quantity of the starting egg white solution to be treated is very small, for example, 500 kg/one batch, the resin tank 15 may be replaced with an ordinary tank such as a hopper. In this case, the resin received in the tank may be made to be transferable by manual operation to the adsorption tank. In such a case, a great saving can be made in the installation cost.

In the above described example, the receptacle 10 for the egg white to be treated is also used as reservoir for lysozyme-free egg white solution. This is not an essential requirement; a reservoir may be provided separately from the receptacle 10.

Further, in the above described example, the resin discharge pipe 13a of the adsorption tank 1 is connected at only one position above the strainer 3A at the lower portion of the adsorption tank and in the vicinity of said strainer. It is also possible to provide such discharge pipes at several positions on the upper side wall of the adsorption tank 1. For example, so as to function also as the liquid discharge pipe 6b connected similarly to the side wall, the pipes can be connected to each other. That is, so as to be capable of discharging substantially completely the mixture of the resin and the water, the resin discharge pipe comprises at least one pipe connected at a position above the strainer at the lower portion of the adsorption tank as described above and others connectable to the centrifugal pump by change-over operations of valves.

On the other hand, the liquid discharge pipe is constituted by a pipe which is connected to the side wall of the adsorption tank at a position to deliver the lysozyme-free egg white solution to the reservoir (e.g., receptacle 10) without flowing out of the resin, and a pipe connected at a position lower than the strainer, preferably at the bottom, of the adsorption tank, these pipes being connectable to the positive displacement pump by change-over operations of valves.

As described above, unique features of the present invention are that particular attention has been paid to ion-exchange treatment according to the batch process in the operation of adsorption of egg white lysozyme, in which the resin required per egg white solution can be far smaller than that in the ion-exchange treatment acccording to the columnar process, and that two kinds of pumps with different mechanisms have been utilized in adopting the batch process, whereby transfer of the liquid and the resin out of and into the adsorption tank, which has been deemed to be inefficient, can be carried out very smoothly.

That is, in one aspect, a singular feature of the apparatus according to the present invention resides in the provision of a structure in which liquid discharge pipes are connected to the lower part of the adsorption tank below the strainer and to the side wall of the this tank at a position higher than the strainer, respectively, and connected to a positive displacement pump, whereby delivery of egg white solution after removal of lysozyme or salt solution having lysozyme dissolved therein can be performed without difficulty. In another aspect, a characteristic feature of the invention resides in the provision of a structure in which the resin discharge pipe is connected to the adsorption tank in the vicinity of and above the strainer and connected to a centrifugal pump, whereby the resin can be delivered smoothly simultaneously with prevention of damage of the resin caused by delivery.

Accordingly, with the use of this apparatus of the present invention, pump delivery of solutions and resin is made possible, and it is not necessary to use pressurized air as in the prior art. Consequently, the tank itself may have a wall thickness reduced correspondingly, and the structure of the apparatus as a whole can be simplified. Further, smooth discharge and intake of solutions or resin makes it possible to use the adsorption tank also as an extraction tank, with the result that the resin tank useable, alternatively as an extraction tank, can be made compact and simple. For these reasons, the apparatus according to the present invention can be manufactured at lower cost than that of the prior art. Further, it is also a very suitable apparatus for small-scale production of lysozyme by treatment of a small amount of egg white solution. At the same time, by combination with the resin tank as an extraction tank, it may also be used as a semi-continuous treatment apparatus.

What we claim is:

1. An apparatus for collecting lysozyme in egg white by adsorption, comprising:
   a lysozyme adsorption tank equipped therein with first stirring means for stirring an egg white solution and an ion-exchange resin and having a strainer provided in a lower portion thereof;
   a receptacle having an inlet and an outlet;
   a water and resin tank having second stirring means and a strainer positioned therein;
   a first liquid discharge pipe extending from a bottom of said lysozyme adsorption tank;
   a second liquid discharge pipe extending from a side wall of said lysozyme adsorption tank at a location for withdrawing liquid from above the resin when the resin is at rest, said first and second liquid discharge pipes comprising means for draining off liquid from said lysozyme adsorption tank;
   positive displacement pump means, an inlet of said positive displacement pump means being in communication with said first and second liquid discharge pipes;
   a third liquid discharge pipe communicating an outlet of said positive displacement pump means with said inlet of said receptacle for transferring an egg white solution to said receptacle after removal of lysozyme;
   a first resin discharge pipe extending from a lower portion of said side wall of said lysozyme adsorption tank at a location above said strainer;
   a second resin discharge pipe extending from a lower portion of said water and resin tank;
   centrifugal pump means, an inlet of said centrifugal pump means being in fluid communication with said first and second resin discharge pipes;
   third and fourth resin discharge pipes in fluid communication with an outlet of said centrifugal pump means and respectively communicating said outlet of said centrifugal pump means with inlets of said water and resin tank and said lysozyme adsorption tank; and
   valve means for enabling the selective transfer of liquid by said centrifugal pump means from said lysozyme adsorption tank to said water and resin tank and from said water and resin tank to said lysozyme adsorption tank through said first, second, third and fourth resin discharge pipes.

2. An apparatus according to claim 1, wherein the strainer provided in the lysozyme adsorption tank has a structure which is freely detachable from said tank from the outside.

3. An apparatus according to claim 1, wherein said receptacle contains a starting egg white solution, said receptacle having a starting-material feed pipe connected thereto for transferring the starting egg white solution to said adsorption tank via the starting-material feed pipe.

4. An apparatus according to claim 3, further comprising a positive displacement pump means connected to the starting-material feed pipe for transferring the starting egg white solution to said adsorption tank.

5. An apparatus according to claim 1, further comprising a water supply pipe and a drain pipe provided internally at the upper part of the lysozyme adsorption tank.

6. An apparatus according to claim 1, further comprising a water supply pipe provided at the bottom of the lysozyme adsorption tank.

7. An apparatus as claimed in claim 1, said lysozyme adsorption tank further comprising an overflow drain disposed in an upper portion thereof for draining off liquid from said lysozyme adsorption tank whenever the level of liquid in said lysozyme adsorption tank reaches said overflow drain.

* * * * *

UNITED STATES PATENT AND TRADEMARK OFFICE
CERTIFICATE OF CORRECTION

PATENT NO. : 4,705,755

DATED : 11-10-87

INVENTOR(S) : Mineo Hasegawa and Kitao Ozaki

It is certified that error appears in the above-identified patent and that said Letters Patent is hereby corrected as shown below:

-- Priority information is incorrectly recorded.
   It should read:
      May 31, 1982 [JP] JAPAN............57-92512--

Signed and Sealed this

Tenth Day of May, 1988

Attest:

DONALD J. QUIGG

Attesting Officer

Commissioner of Patents and Trademarks